US011629372B2

(12) United States Patent
Xu et al.

(10) Patent No.: US 11,629,372 B2
(45) Date of Patent: Apr. 18, 2023

(54) RANDOM HETEROPOLYMERS PRESERVE PROTEIN FUNCTION IN FOREIGN ENVIRONMENTS

(71) Applicant: The Regents of the University of California, Oakland, CA (US)

(72) Inventors: Ting Xu, Berkeley, CA (US); Brian Panganiban, Berkeley, CA (US); Tao Jiang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 279 days.

(21) Appl. No.: 16/907,284

(22) Filed: Jun. 21, 2020

(65) Prior Publication Data

US 2020/0318154 A1 Oct. 8, 2020

Related U.S. Application Data

(63) Continuation of application No. PCT/US2019/013546, filed on Jan. 14, 2019.

(60) Provisional application No. 62/618,537, filed on Jan. 17, 2018.

(51) Int. Cl.
*C12Q 1/34* (2006.01)
*C08L 89/00* (2006.01)
*C12N 9/16* (2006.01)
*G01N 33/68* (2006.01)

(52) U.S. Cl.
CPC .............. *C12Q 1/34* (2013.01); *C08L 89/00* (2013.01); *C12N 9/16* (2013.01); *C12Y 301/08001* (2013.01); *G01N 33/68* (2013.01); *C08L 2203/02* (2013.01)

(58) Field of Classification Search
CPC ...... C12N 9/16; C12N 9/14; C12Y 301/08001; C12Q 1/34
See application file for complete search history.

(56) References Cited

U.S. PATENT DOCUMENTS

2016/0279251 A1 9/2016 Stayton et al.

FOREIGN PATENT DOCUMENTS

WO   WO2006138099 A2 * 12/2006

OTHER PUBLICATIONS

Brian Matibag Panganiban, Generating protein-functionalized nanomaterials via rationally designed statistically random heteropolymers. A Dissertation for PhD, University of California, Berkley, Sep. 2016, p. 1-145. (Year: 2016).*
Kim et al. Enhanced activity and stability of organophosphorus hydrolase via interaction with an amphiphilic polymer. Chem. Commun. (2014), 50(40), 5345-5348. (Year: 2014).*
Mills et al. Complex coacervate core micelles for the dispersion and stabilization of organophosphate hydrolase in organic solvents. Langmuir (2016), 32: 13367-13376. (Year: 2016).*
International Search Report, Written Opinion, in priority application PCT/US19/13546.
Panganiban et al, Random heteropolymers preserve protein function in foreign environments, Science 359, 1239-1243 (2018).

* cited by examiner

*Primary Examiner* — Iqbal H Chowdhury
(74) *Attorney, Agent, or Firm* — Richard Aron Osman

(57) ABSTRACT

Compositions comprise statistically random heteropolymers complexed with active proteins, and are formulated and used in stimuli-responsive materials and nanoreactors composed of proteins and synthetic materials.

17 Claims, No Drawings

RANDOM HETEROPOLYMERS PRESERVE PROTEIN FUNCTION IN FOREIGN ENVIRONMENTS

This invention was made with government support under Grant Numbers W911NF-13-1-0232 and W911NF-16-1-0405 awarded by the Department of Defense, Army Research Office. The government has certain rights in the invention.

INTRODUCTION

The successful incorporation of active proteins into synthetic polymers could lead to a new class of materials with functions found only in living systems. However, proteins rarely function under the conditions suitable for polymer processing. Based on the analysis of trends in protein sequences and characteristic chemical patterns on protein surfaces, we design multi-monomer random heteropolymers to mimic intrinsically disordered proteins for protein solubilization and stabilization in non-native environments. The heteropolymers, with optimized composition and statistical monomer distribution, enable cell-free synthesis of membrane proteins with proper protein folding for transport and enzyme-containing plastics for toxin bioremediation. Controlling the statistical monomer distribution in a heteropolymer, rather than the specific monomer sequence, provides a new strategy to interface with biological systems for protein-based biomaterials.

SUMMARY OF THE INVENTION

We disclose optimization of statistically random heteropolymers (SRHPs) to act as synthetic chaperones and effectively disperse proteins in organic solvents without compromising protein structure and enzymatic activity. Using SRHPs, we have been able to retain most (about 80%) enzymatic activity in horseradish peroxidase (HRP) and most (close to 100%) fluorescence in green fluorescent protein (GFP) when solubilized in organic solvents like toluene. Furthermore, we demonstrate that nanoreactors with encapsulated proteins can enzymatically interact with substrates in organic media as well as substrates encapsulated in reverse micelles. Lastly, we show how a protein's ability to solubilize in organic solvents allows for unique processing techniques, such as being able to electrospin HRP into hydrophobic nanofiber mats.

The invention provides compositions comprising statistically random heteropolymers complexed with active proteins, and formulation and use in stimuli-responsive materials and nanoreactors composed of proteins and synthetic materials.

In one aspect the invention provides a composition comprising a complex of an active protein and statistically random heteropolymers (SRHPs) in an organic solvent, such as 2-propanol, acetone, acetonitrile, chloroform, dichloromethane, dimethyl sulfoxide, ethyl acetate, hexane, methanol, tetrahydrofuran, and toluene, particularly a solvent that would otherwise effectively denature or render inactive the protein if uncomplexed with the SRHPs.

In embodiments:
the heteropolymers disperse in both aqueous and organic media,
the distribution histogram of monomer blocks of the heteropolymers decrease in normalized frequency from block size 1, wherein block size 10 (or 12) has a normalized frequency of less than 1% (and block size 1 has a normalized frequency of 5-20%);
the protein is an enzyme or fluorescent protein;
the solvent is selected from 2-propanol, acetone, acetonitrile, chloroform, dichloromethane, dimethyl sulfoxide, ethyl acetate, hexane, methanol, tetrahydrofuran, and toluene;
the SRHPs comprising varying ratios a plurality (2-3 or 2-4 or 2-6 or 2-8 or 2-12) of monomers;
the monomers are selected from methyl methacrylate (MMA), oligo(ethylene glycol) methacrylate (OEGMA), 3-sulfopropyl methacrylate potassium salt (3-SPMA) and 2-ethylhexyl methacrylate (2-EHMA); and/or
the SRHPs have a compositional ratio of 5(MMA):2.5(OEGMA):2(2-EHMA):0.5(3-SPMA).

In another aspect the invention provides a method of making a disclosed composition comprising or consisting essentially of: mixing the protein and the SRHPs in an aqueous solution; drying the mixture; resuspending the dried mixture in an organic solvent, forming the composition.

In another aspect the invention provides a method of using a disclosed composition comprising detecting activity of the protein in the composition.

In another aspect the invention provides a composition comprising a complex of an active protein and statistically random heteropolymers (SRHPs) in a protein expression system, wherein the protein is being expressed and incorporated in the complex.

In embodiments:
the complex enhances activity of the protein, compared an expression system without the SRHPs; and/or the expression system is a cell-free system.

In another aspect the invention provides a method of making a disclosed composition comprising or consisting essentially of: expressing the protein in the presence of the SRHPs wherein the SRHPs and protein form the complex.

In another aspect the invention provides a method of using a disclosed composition comprising or consisting essentially of contacting the complex with a liposome under conditions wherein the protein relocates from the complex to the liposome, such as wherein the protein locates to the liposome in form of an active, transmembrane protein.

The invention encompasses all combination of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Nature's building blocks, such as proteins and biomachinery, have many features unmatched by synthetic counterparts, including chemical diversity, hierarchical structure, programmed system dynamics, and efficient energy conversion. Despite years of effort to stabilize proteins outside of their native environments, there has been limited development in interfacing biological and synthetic components without compromising their structures and inherent functions. Non-aqueous enzymology via reverse micelles can only maintain a fraction (<20%) of native activity (1); amphipols solubilize membrane proteins, but not for water-soluble proteins in organic solvents (2); polymer-conjugation relies on accessibility of protein functional groups (3); and sol-gel confinement limits protein accessibility and post integration (4).

A chaperone-like polymeric shell outside of a protein may effectively improve protein solubility and stability in organic solvents by providing a barrier to resist both organic solvent exposure and protein conformational change. To form such a nanoscopic polymeric shell, protein-polymer interactions need to be strong enough to favor adsorption, yet soft enough to not outcompete the forces governing protein folding. The structure and activity of natural building blocks are governed by multiple non-covalent interactions that are subject to change with small perturbations (5). When a homopolymer is conjugated to a protein surface, monomer-amino acid interactions can affect protein folding (6, 7) and deform the polymer chain conformation (8). In nature, intrinsically disordered proteins adopt local chain conformations, often achieved by multiple weak binding sites, and mediate various processes (9, 10). Amphiphilic heteropolymers mimicking disordered proteins may offer a versatile approach for protein solubilization and stabilization given the diversity and complexity of proteins.

Protein surfaces are chemically diverse and heterogeneous. Surface analysis of folded water-soluble proteins based on hydrophobicity or charge shows characteristic patch size distributions. The typical patch size is 1-2 nm in diameter with an inter-patch distance of 1-2 nm. Sequence analysis of water-soluble proteins, performed by assigning amino acids as either hydrophilic or hydrophobic using glycine as the reference (11), shows that the block length of amino acids with similar hydrophobicity tends to be less than 10. Matching the statistical chemical pattern has been shown to be critical in de novo protein design (12, 13) and in modulating polymer/surface interactions (14). Rather than synthesizing sequence specific polymers (15), synthetic heteropolymers with similar chemical features and spatial distributions of side chains to match the surface pattern of natural proteins may behave like disordered proteins.

Recent developments in reversible de-activation radical polymerization make it feasible to synthesize random heteropolymers with reliable control over the statistical monomer distribution (16-18). Four methacrylate-based monomers are selected to impart chemical diversity in heteropolymers and to optimize short-range polymer-protein interactions: methyl methacrylate (MMA), oligo(ethylene glycol) methacrylate (OEGMA, $M_n$=500 Da), 2-ethylhexyl methacrylate (2-EHMA), and 3-sulfopropyl methacrylate potassium salt (3-SPMA). MMA is to tailor the overall hydrophobicity for protein solubilization, to anchor the chain at the polar-nonpolar interface and to reduce the entropic penalty associated with adjusting its local conformation. OEGMA is to leverage the well-known ability of poly(ethylene glycol) (PEG) to stabilize proteins. 2-EHMA and 3-SPMA are chosen to interact with the hydrophobic and positive charged residues on the protein surface, respectively. The selection of the monomer ratio is guided by the calculated solubility parameters (19, 20) and through experimental screenings to achieve polymer dispersion in both aqueous and organic media with the best retention in enzyme activity. Our best performing heteropolymer, called "RHP", has a compositional ratio of 5(MMA):2.5(OEGMA):2(2-EHMA):0.5(3-SPMA). Using the well-established Mayo-Lewis equation, we estimate the statistical monomer distribution along the RHP chains (21, 22). The histogram of monomer block size confirms the absence of long blocks of the same monomer that could interfere with native protein structure. The RHP used has a number-average molecular weight of ~30 kDa and a dispersity of 1.3. At least 12 batches of RHP were synthesized with excellent reproducibility.

Computational studies are performed on mixtures of a common enzyme, horseradish peroxide (HRP), and RHP in both an aqueous buffer solution and toluene to elucidate the polymer-protein adsorption mechanism. Explicit solvent all-atom molecular dynamics (MD) simulations were performed using the CHARMM 36 potential (Supplementary, Section S3). The RHPs are built with compositions and degrees of polymerization close to the corresponding experimental values. Simulation snapshots of the RHP/HRP mixture in toluene and in water show that in water, RHP and HRP are loosely complexed and only ~40% of HRP surface is covered by RHP, in line with the experimental observations that RHP is soluble in water. However, the HRP surface is fully covered by RHPs in toluene; the complex is stable and no protein structure change is observed over the simulation duration of 0.6 μs. The radial distribution of RHPs around the protein's center-of-mass is calculated in toluene and in water. In toluene, the hydrophilic monomers of the polymer (OEGMA and 3-SPMA) point inward, adjacent to the protein, while the hydrophobic monomers (MMA and 2-EHMA) are located on the outside, in contact with the toluene. In contrast, the favored orientations of the RHP side-chains become weaker in water. These results indicate that, once positioned close to the protein surface, the RHPs can adjust their conformations to maximize protein-polymer interactions, which correlates well with our hypothesis. Correlations between the protein surface groups and their nearest monomer neighbors are computed by categorizing ALA, VAL, ILE, LEU, MET, PHE, TYR, TRP, GLY and PRO amino acids as hydrophobic and the others as hydrophilic. Approximately 70% of the protein surface is covered by the hydrophilic monomers; 50±4% originates from hydrophilic monomer-hydrophilic amino acid interactions, contributing −800±300 kJ/mol to the energy. This shows the significance of the local protein surface-polymer interactions in stabilizing the protein structure. The shell formed by the polymer around the HRP core in organic solvents improves protein solubility and stability by providing a barrier to resist both organic solvent exposure and protein conformational change.

The role of the RHP's composition on their ability to encapsulate the protein in water and toluene is investigated using a coarse-grained model based on the data gathered from all-atom MD simulations and experiments (Supplementary, Section S4). A representative snapshot of the RHP fully encapsulating the protein was performed. The surface coverage increases as the attraction strength between the adsorbing monomers and protein attractive sites, $\varepsilon_{Hh}$, increases for all solvent selectivity conditions (captured by the attraction strength between the polymer solvophobic beads, $\varepsilon_{hh}$). For sufficiently high $\varepsilon_{hh}$, there exists an optimal value of the fraction of absorbed monomers ($\phi_A$) that maximizes the surface coverage. The spatial correlations between the adsorbing monomers and the protein attractive sites demonstrate that the RHPs tend to adopt energetically favored conformations once in contact with the protein to compensate for the entropic penalty associated with confinement to the surface (23).

We experimentally test our hypothesis that RHP is capable of interacting with proteins and mediating their interactions with the local environment. We performed cell-free synthesis of membrane proteins that eliminates potential interference or assistance from the host cell physiology for protein folding and lipid insertion during translation (24). Once the plasmids for a model transmembrane protein, oligopeptide/proton symporter PepTso or GFP-tagged aquaporin Z (AqpZ), are added, the translation and folding status of the membrane protein is scored based on fluorescence intensity of a C-terminus fused green fluorescent protein (GFP). Western blotting analysis using anti-GFP antibodies confirmed PepTso-GFP expression regardless of the presence of RHP. Without RHP, no GFP fluorescence is detected indicating the protein folding is not correct to gain GFP fluorescence (25). Control experiments using amphipol (A8-35) that is effective in stabilizing membrane proteins post protein expression show little GFP fluorescence for aqpZ (2). However, there is a ca. 15-fold increase in GFP fluorescence when PepTso-GFP or AqpZ is expressed in the presence of RHP at a RHP:ribosome mole ratio of 50:1. The resultant GFP fluorescence is over an order of magnitude higher than that of commonly used liposome. To further verify the protein folding, the cell-free synthesized PepTso is reconstituted in liposomes, and tested in a pyranine-based proton transport assay (26). Proton transport is detected by adding valinomycin to the outer solution containing a dipeptide, Ala-Ala. The cell-free synthesized PepTso, in the presence of RHP, can fold properly to retain transport function in a lipid environment. Thus, RHP is able to chaperone proper protein folding and solubilize membrane proteins in aqueous solution, but will not outcompete the protein-lipid interaction, interfere with lipid insertion, or compromise channel transport function.

We investigated protein dispersion and stabilization in organic solvents, a requirement to interface proteins with synthetic building blocks toward protein-based materials. Previous non-aqueous enzymology studies of HRP observed over 100-fold activity reduction in hydrophobic solvents that can extract the heme cofactor (27). For all studies, proteins and RHPs are first co-solubilized in deionized water, lyophilized, and subsequently re-suspended in solvents. The RHP/HRP complexes are readily soluble in common solvents for material synthesis and processing such as toluene and chloroform. TEM results show that RHP/HRP complexes form nanoparticles with a diameter of ~50-60 nm. Fourier transform-infrared spectroscopy (FT-IR) spectra are collected after dissolving RHP/HRP complexes in toluene over 24 hours. The amide I band and its corresponding negative second derivative reveal minimal change in the HRP's secondary structure in toluene. No significant change is observed in the UV-visible spectra of the heme co-factor in HRP over 24 hours, confirming the retention of HRP tertiary structure and stability of the heme binding pocket in toluene, critical for enzymatic activity. To evaluate the retention of the HRP activity after suspension in toluene, aliquots of RHP/HRP toluene solution are dispersed in aqueous solution to perform colorimetric assay. With the presence of RHP, ~80% of HRP native activity is maintained after 24 hours suspended in toluene. This is several orders of magnitude higher than HRP alone in non-aqueous media and at least 4 times higher than the best reported value using molecular and/or polymeric surfactants (1).

We explore the versatility and universality of RHP by extending the study to other proteins. PEGylation is effective for protein dispersion and stabilization, but is not effective for proteins with a small number of functionalizable groups, such as glucose oxidase (GOx) (28). The PEGylation is sufficient for GOx dispersion, but the proteins retain less than 10% of native activity after 2 hours. In contrast, RHP/GOx shows ~50% of native activity after 24 hours of storage in toluene. Proteins with different structure, such as β-barrel GFP, are also tested. After RHP/GFP complex is solubilized in organic solvents, there is no detectable shift in fluorescent emission peak maxima and minimal decrease in the emitted fluorescence over 24 hours. These results confirm that the environment in the β-barrel interior remains the same, and indicate substantial exclusion of toluene penetration into the protein core.

The RHP-enabled protein solubilization and stabilization can lead to technologically relevant protein-based materials. Organophosphorus hydrolase (OPH) is chosen for its excellent ability to degrade organophosphates, commonly used as insecticides and chemical warfare agents (29). However, OPH becomes inactive even in its partially folded dimeric state (30) and organophosphates typically have poor solubility in aqueous solution. There is a need to retain OPH activity while co-solubilized with organophosphates to realize on-demand bioremediation for these acute toxins. OPH activity is evaluated using a 10 mM preparation of the well-known pesticide, methyl parathion (MP). RHP/OPH can be readily solubilized in toluene and chloroform and re-suspended in buffer solution. RHP/OPH retains 80±5.6% (N=3) of the initial OPH activity after 24 hour suspension in toluene. When methyl parathion is co-dissolved with RHP/OPH in toluene, dried, and assayed, the OPH activity is over 7 times higher than that of pure OPH in aqueous solution. This is attributed to the higher substrate concentration in toluene and RHP's ability to stabilize OPH in both aqueous and organic media. The successful dispersion and stabilization of RHP/OPH complexes enables co-processing of OPH and synthetic polymers. Fiber mats based on either polyethylene oxide (PEO) or PMMA were prepared via electrospinning and tested for bioremediation. Both fiber mats are active and degrade MP, weighing approximately one tenth of the total fiber mat, in a few minutes. In particular, when the RHP/OPH/PEO fiber mat is soaked in MP-containing toluene solution and assayed in buffer, the hydrolysis by-products can be trapped for easy removal. This enables in situ toxin remediation without pre-processing, transfer, or contact with the agent prior to and post detoxification.

Our studies confirm that random heteropolymers designed based on statistical monomer distribution are effective at maintaining protein function in foreign environments. We demonstrated successful cell-free synthesis of membrane proteins with proper folding, and retention of protein activity in organic solvents for a wide range of proteins These hybrid materials not only take advantages of precision and efficiency of natural building blocks, but also enable reactions and processes on demand where common chemistry necessities are unavailable.

REFERENCES

1. A. M. Klibanov, Improving enzymes by using them in organic solvents. *Nature* 409, 241-246 (2001).
2. J. L. Popot et al., Amphipols: polymeric surfactants for membrane biology research. *Cellular and Molecular Life Sciences* 60, 1559-1574 (2003).

3. E. M. Pelegri-O'Day, H. D. Maynard, Controlled Radical Polymerization as an Enabling Approach for the Next Generation of Protein-Polymer Conjugates. *Accounts of Chemical Research* 49, 1777-1785 (2016).
4. R. B. Bhatia, C. J. Brinker, A. K. Gupta, A. K. Singh, Aqueous sol-gel process for protein encapsulation. *Chem Mater* 12, 2434-2441 (2000).
5. K. A. Dill, Dominant Forces In Protein Folding. *Biochemistry* 29, 7133-7155 (1990).
6. J. Y. Shu et al., Amphiphilic Peptide-Polymer Conjugates Based on the Coiled-Coil Helix Bundle. *Biomacromolecules* 11, 1443-1452 (2010).
7. N. Dube, A. D. Presley, J. Y. Shu, T. Xu, Amphiphilic Peptide-Polymer Conjugates with Side-Conjugation. *Macromolecular Rapid Communications* 32, 344-353 (2011).
8. R. Lund, J. Shu, T. Xu, A Small-Angle X-ray Scattering Study of alpha-helical Bundle-Forming Peptide-Polymer Conjugates in Solution: Chain Conformations. *Macromolecules* 46, 1625-1632 (2013).
9. H. J. Dyson, P. E. Wright, Intrinsically unstructured proteins and their functions. *Nat Rev Mol Cell Bio* 6, 197-208 (2005).
10. Z. R. Liu, Y. Q. Huang, Advantages of proteins being disordered. *Protein Sci* 23, 539-550 (2014).
11. O. D. Monera, T. J. Sereda, N. E. Zhou, C. M. Kay, R. S. Hodges, Relationship of sidechain hydrophobicity and α-helical propensity on the stability of the single-stranded amphipathic α-helix. *Journal of Peptide Science* 1, 319-329 (1995).
12. W. F. DeGrado, C. M. Summa, V. Pavone, F. Nastri, A. Lombardi, De novo design and structural characterization of proteins and metalloproteins. *Annual Review of Biochemistry* 68, 779-819 (1999).
13. D. A. Moffet, M. H. Hecht, De novo proteins from combinatorial libraries. *Chem Rev* 101, 3191-3203 (2001).
14. P. Mansky, Y. Liu, E. Huang, T. P. Russell, C. J. Hawker, Controlling polymer-surface interactions with random copolymer brushes. *Science* 275, 1458-1460 (1997).
15. J. F. Lutz, M. Ouchi, D. R. Liu, M. Sawamoto, Sequence-Controlled Polymers. *Science* 341, 628-631 (2013).
16. J. Chiefari et al., Living free-radical polymerization by reversible addition-fragmentation chain transfer: The RAFT process. *Macromolecules* 31, 5559-5562 (1998).
17. G. Moad, E. Rizzardo, S. H. Thang, Toward living radical polymerization. *Accounts of Chemical Research* 41, 1133-1142 (2008).
18. A. E. Smith, X. Xu, C. L. McCormick, Stimuli-responsive amphiphilic (co)polymers via RAFT polymerization. *Progress in Polymer Science* 35, 45-93 (2010).
19. A. F. M. Barton, *Handbook of Polymer-Liquid Interaction Parameters and Solubility Parameters*. (Taylor & Francis, 1990).
20. J. N. Israelachvili, *Intermolecular and Surface Forces*. (Elsevier Science, 2015).
21. B. G. Manders, W. Smulders, A. M. Aerdts, A. M. vanHerk, Determination of reactivity ratios for the system methyl methacrylate-n-butyl methacrylate. *Macromolecules* 30, 322-323 (1997).
22. F. R. Mayo, F. M. Lewis, Copolymerization I A basis for comparing the behavior of monomers in copolymerization, the copolymerization of styrene and methyl methacrylate. *J Am Chem Soc* 66, 1594-1601 (1944).
23. T. Ge, M. Rubinstein, Strong selective adsorption of polymers. *Macromolecules* 48, 3788-3801 (2015).
24. D. Schwarz et al., Preparative scale expression of membrane proteins in *Escherichia coli*-based continuous exchange cell-free systems. *Nat Protoc* 2, 2945-2957 (2007).
25. A. Muller-Lucks, S. Bock, B. H. Wu, E. Beitz, Fluorescent In Situ Folding Control for Rapid Optimization of Cell-Free Membrane Protein Synthesis. *Plos One* 7, (2012).
26. J. L. Parker, J. A. Mindell, S. Newstead, Thermodynamic Evidence for a dual Transport Mechanism in a POT Peptide Transporter. *eLife* 3, (2014).
27. A. M. Klibanov, Why are enzymes less active in organic solvents than in water? *Trends in Biotechnology* 15, 97-101 (1997).
28. A. D. Presley, J. J. Chang, T. Xu, Directed co-assembly of heme proteins with amphiphilic block copolymers toward functional biomolecular materials. *Soft Matter* 7, 172-179 (2011).
29. B. K. Singh, A. Walker, Microbial degradation of organophosphorus compounds. *Ferns Microbiol Rev* 30, 428-471 (2006).
30. J. K. Grimsley, J. M. Scholtz, C. N. Pace, J. R. Wild, Organophosphorus hydrolase is a remarkably stable enzyme that unfolds through a homodimeric intermediate. *Biochemistry* 36, 14366-14374 (1997).
31. S. Perrier, P. Takolpuckdee, J. Westwood, D. M. Lewis, Versatile Chain Transfer Agents for Reversible Addition Fragmentation Chain Transfer (RAFT) Polymerization to Synthesize Functional Polymeric Architectures. *Macromolecules* 37, 2709-2717 (2004).
32. B. Hess, C. Kutzner, D. van der Spoel, E. Lindahl, GROMACS 4: Algorithms for Highly Efficient, Load-Balanced, and Scalable Molecular Simulation. *J. Chem. Theory Comput.* 4, 435-447 (2008).
33. P. Bjelkmar, P. Larsson, M. A. Cuendet, B. Hess, E. Lindahl, Implementation of the CHARMM Force Field in GROMACS: Analysis of Protein Stability Effects from Correction Maps, Virtual Interaction Sites, and Water Models. *Journal of Chemical Theory and Computation* 6, 459-466 (2010).
34. J. B. Klauda et al., Update of the CHARMM All-Atom Additive Force Field for Lipids: Validation on Six Lipid Types. *J. Phys. Chem. B* 114, 7830-7843 (2010).
35. K. Vanommeslaeghe et al., CHARMM General Force Field: A Force Field for Drug-Like Molecules Compatible with the CHARMM All-Atom Additive Biological Force Fields. *J. Comput. Chem.* 31, 671-690 (2010).
36. W. Yu, X. He, K. Vanommeslaeghe, A. D. MacKerell, Extension of the CHARMM General Force Field to Sulfonyl-Containing Compounds and its Utility in Biomolecular Simulations. *Journal of Computational Chemistry* 33, 2451-2468 (2012).
37. J. Huang et al., CHARMM36m: An Improved Force Field for Folded and Intrinsically Disordered Proteins. *Nature methods* 14, 71-73 (2017).
38. L. Martinez, R. Andrade, E. G. Birgin, J. M. Martinez, PACKMOL: A Package for Building Initial Configurations for Molecular Dynamics Simulations. *J. Comput. Chem.* 30, 2157-2164 (2009).
39. T. Darden, D. York, L. Pedersen, Particle Mesh Ewald: An N·log(N) Method for Ewald Sums in Large Systems. *J. Chem. Phys.* 98, 10089-10092 (1993).
40. U. Essmann et al., A Smooth Particle Mesh Ewald Method. *J. Chem. Phys.* 103, 8577-8593 (1995).
41. B. Hess, P-LINCS: A Parallel Linear Constraint Solver for Molecular Simulation. *J. Chem. Theory Comput.* 4, 116-122 (2008).

42. B. Hess, H. Bekker, H. J. C. Berendsen, J. G. E. M. Fraaije, LINCS: A Linear Constraint Solver for Molecular Simulations. *J. Comput. Chem.* 18, 1463-1472 (1997).
43. A. Laio, M. Parrinello, Escaping Free-Energy Minima. *Proceedings of the National Academy of Sciences of the United States of America* 99, 12562-12566 (2002).
44. A. Barducci, M. Bonomi, M. Parrinello, Metadynamics. *Wiley Interdisciplinary Reviews: Computational Molecular Science* 1, 826-843 (2011).
45. Y. Sugita, Y. Okamoto, Replica-Exchange Molecular Dynamics Method for Protein Folding. *Chemical Physics Letters* 314, 141-151 (1999).
46. W. Humphrey, A. Dalke, K. Schulten, VMD: Visual Molecular Dynamics *J. Mol. Graphics* 14, 33-38 (1996).
47. A. Arkhipov, P. L. Freddolino, K. Schulten, Stability and Dynamics of Virus Capsids Described by Coarse-Grained Modeling. *Structure* 14, 1767-1777 (2006).
48. A. Arkhipov, Y. Yin, K. Schulten, Four-Scale Description of Membrane Sculpting by BAR Domains. *Biophysical Journal* 95, 2806-2821 (2008).
49. S. Plimpton, Fast Parallel Algorithms for Short-Range Molecular Dynamics. *Journal of Computational Physics* 117, 1-19 (1995).
50. A. Bunker, B. Dünweg, Parallel Excluded Volume Tempering for Polymer Melts. *Physical Review* E 63, 016701 (2000).
51. Y. Avnir, Y. Barenholz, pH Determination by Pyranine: Medium-Related Artifacts and Their Correction. *Anal Biochem* 347, 34-41 (2005).

Supplementary Materials

Section S1. Protein Analysis

S1.1 Analysis of Protein Surface Using PyMOL 1.5.0.3

Horseradish peroxidase (HRP), glucose oxidase (GOx), green fluorescent protein (GFP), and α-chymotrypsin (α-CT) crystal structures—1H55, 1CF3, 2HRW, and 1YPH respectively—were obtained from the Protein Data Bank. PyMOL was used to simplify protein surfaces as non-charged hydrophilic, hydrophobic, cationic, or anionic patches. Patches were approximated as circles with distinct diameters, and distances between chemically-like patches were measured using straight lines, from the center of one patch to the center of a neighboring patch. Measurements were binned to the closest whole number, and frequencies were normalized by the frequency of the mode. The histograms of diameter and distance of charged patches were plotted.

S1.2 Analysis of Protein Sequence Based on Binary Hydrophobicity

The program reads in an amino acid sequence from a protein database (PDB) file, and assigns each amino acid a value of 0 or 1. All amino acids more hydrophilic than glycine are assigned a value of 0, while all amino acids more hydrophobic than glycine including glycine are assigned a value of 1. The scale is a binary adaptation of the scale established by Monera et al. (11). Then, starting from the beginning of the chain, it counts the distance between two hydrophilic residues to determine the size of that hydrophobic block. This is repeated until the whole chain has been analyzed.

Section S2. RHP Synthesis and Characterization

S2.1. Synthesis of RHP by RAFT Polymerization

Methyl methacrylate (1, 99%, Aldrich), ethylene glycol methyl ether methacrylate (2, 99%, $M_n$=500 g/mol, Aldrich), and 2-ethylhexyl methacrylate (3, 98%, Aldrich) were passed through a short column of neutral alumina to remove inhibitor before use. 3-Sulfopropyl methacrylate potassium salt (4, 98%, Aldrich) and solvents with the purest grades (Aldrich) were used as received. S-methoxycarbonylphenylmethyl dithiobenzoate (5) RAFT chain transfer agent was synthesized as described previously (31).

A solution of 1 (513 mg, 5.13 mmol), 2 (1280 mg, 2.56 mmol), 3 (403 mg, 2.03 mmol), 4 (123 mg, 0.50 mmol), and 5 (11 mg, 0.04 mmol) in N,N-dimethylformamide (3.2 mL) was degassed by three freeze-pump-thaw cycles before being sealed off under vacuum. After 20 h at 60° C., the polymerization media was diluted in dichloromethane, precipitated in diethyl ether and dried under vacuum. The resulting polymer was dissolved in tetrahydrofuran and dialyzed against a 1:1 mixture of tetrahydrofuran and water for 3 days and against pure water for 2 days using dialysis membranes with a molecular weight cut-off of 6,000-8,000 g/mol (Spectrum Laboratories Inc.). Dialysis solutions were renewed every day. Finally, the remaining aqueous solution was freeze dried, producing a viscous pink polymer.

S2.2. RHP Sequence Simulation and Analysis

S2.2.1. Simulations of RHP Sequences

We performed Monte-Carlo style simulations of the copolymerizations. We define the total number of monomers, their relative concentration ratios, and the monomer to RAFT ratio. Then, borrowing from the Mayo-Lewis copolymerization equation (Eq. 51, S2) (22), the reactivity ratios for each monomer with itself, along with each other monomer are inputted. Finally, a target percent conversion is chosen that determines the degree of polymerization of the polymers simulated.

Mayo-Lewis Equation:

$$\frac{d[M_1]}{d[M_2]} = \frac{[M_1](r_1[M_1] + [M_2])}{[M_2]([M_1] + r_2[M_2])} \tag{S1}$$

where [$M_x$] is the concentration of monomer x, and $$r_x = \frac{K_{xy}}{K_{xx}}$$

Instantaneous Form:

$$F_1 - 1 - F_2 - \frac{r_1 f_1^2 + f_1 f_2}{r_1 f_1^2 + 2 f_1 f_2 + r_2 f_1^2} \tag{S2}$$

where $f_x$ is the mole fraction of monomer x in the feed, and $F_x$ is the mole fraction of monomer x in the copolymer.

The simulation is broken up into three steps: (i) Beginning, (ii) Growth, and (iii) Ending. A brief discussion of each step is outline below.

Beginning. The first monomer on a given chain is determined based on the relative concentration ratio of that monomer, e.g. if MMA is 50% of the total monomer batch, there is a 50% probability of MMA being the first monomer. Each chain is then initiated by an implied idealized initiator with no preference toward any particular monomer, by randomly choosing one of the monomers taking into account the aforementioned weighted probabilities. This is done for the total number of chains simulated as defined by the monomer to RAFT ratio.

Growth. Each chain is then grown based on the probability for a given monomer to add to the one that precedes it in the simulated chain. First, weighting factors for each chain are established according to the equation w=rx[M] where w is the weighting factor, r is the reactivity ratio for a given monomer pair, and [M] is the current concentration of the monomer being added. These weighting factors are normalized to produce probabilities for each type of addition event to occur. The chain is then grown randomly by one monomer based on the probabilities calculated previously, with the added monomer removed from the total monomer pool. This is completed for all chains, at which point the process loops back to the first propagation step.

Ending. The growth process proceeds until the targeted percent conversion is achieved.

The 4-monomer simulation was performed assuming the reactivity ratios for the methacrylic methylene esters (OEGMA, EHMA, SPMA) to be equal and a reduced value for MMA, as determined by Manders et al. (21) (Table S1). The validity of this assumption on reactivity was supported by the conversion of the individual monomers, as observed by $^{13}$C-NMR, which shows equal consumption of the methacrylic methylene esters (OEGMA, EHMA, SPMA), and a lower conversion of MMA at all global conversions.

S2.3. Characterization of RHP $^1$H NMR and $^1$H-$^{13}$C heteronuclear single quantum coherence (HSQC) 2D NMR spectra were carried out at 363 K with a Bruker Avance III 400 spectrometer (400 MHz for $^1$H and 100 MHz for $^{13}$C) using a 5 mm BBFO+ probe. Quantitative $^{13}$C NMR distortionless enhancement by polarization transfer (DEPT135) spectra were carried out at 363 K and 100 MHz with a Bruker Avance II 400 spectrometer using a 10 mm selective 13C SEX probe. Polymer samples were examined as ca. 15% (w/v) solutions in N,N-dimethylformamide-d$_7$ (DMF-d$_7$). Chemical shift values (δ) are given in ppm in reference to residual hydrogenated solvent. Number average ($M_n$) and weight average ($M_w$) molar masses and dispersity (Đ=$M_w$/$M_n$) of RHP were obtained from size exclusion chromatography (SEC) using a Waters 717 Plus autosampler, a 515 HPLC pump, a 2410 differential refractometer, a 2487 UV-vis detector, a MiniDawn multi-angle laser light scattering (MALLS) detector (measurement angles are 44.7°, 90.0°, and 135.4°) from Wyatt Technology Inc., a ViscoStar viscosity detector from Wyatt, and five Styragel HR columns connected in the following order: 500, 103, 104, 105, and 100 Å. Tetrahydrofuran (THF) was used as the eluent at a flow rate of 1.0 mL/min at room temperature. The results were processed using the Astra 5.4 software from Wyatt Technology Inc.

$^1$H NMR spectra of RHP were used to verify that neither organic solvents nor monomer residuals were present in the final samples. The attribution of NMR signals was performed by comparing the $^1$H NMR, quantitative $^{13}$C NMR and DEPT $^{13}$C NMR, and $^1$H-$^{13}$C HSQC 2D NMR spectra with those of monomers 1, 2, 3, 4 and 2-monomer random copolymers model analogues obtained by the copolymerization of 80 mol % of 1 and 20 mol % of either 2, 3 or 4.

Calculating experimental monomer ratios was performed by comparing the quantitative $^{13}$C NMR spectra integrations of 1 at 51.86 ppm ($I_1$), 2 at 58.43 ppm ($I_2$), 3 at 68.74 ppm ($I_3$) and 4 at 48.77 ppm ($I_4$). Molar ratios of monomers 1 (i), 2 (j), 3 (k) and 4 (l) were calculated using equations S3-S6.

$$i=I_1/(I_1+I_2+I_3+I_4) \quad (S3)$$

$$j=I_2/(I_1+I_2+I_3+I_4) \quad (S4)$$

$$k=I_3/(I_1+I_2+I_3+I_4) \quad (S5)$$

$$l=I_4/(I_1+I_2+I_3+I_4) \quad (S6)$$

RHP composition and SEC data can be found in Table S2.

S2.4. Analysis of Compositional Drift by Varying Conversion

A set of 12 individual batches of RHPs were made and brought to various conversions to examine the possibility of compositional drift. All reagents were purchased from Sigma Aldrich and used without further purification unless specified otherwise. Azobisisobutyronitrile (AIBN) was recrystallized in ethanol prior to use. To remove inhibitors prior to polymerization, methyl methacrylate (1) and 2-ethylhexyl methacrylate (3) were cryodistilled and ethylene glycol methyl ether methacrylate (2) was passed over a column of basic alumina. 3-Sulfopropyl methacrylate potassium salt (4) was used without further purification. Ethyl-2 (phenylcarbanothioylthio)-2-phenylacetate (98%) was purchased from Aldrich and used as received. Three different ratios of monomers to RAFT agent were tested: 572:1, 286:1, 191:1, with four duplicates of each. Reaction times were varied in order to target approximate conversions.

1. 25% Conversion Target (A1, A2, A3, A4)

4 clean 20 mL glass ampules were each charged with 1 (0.501 g, 5.00 mmol), 2 (1.25 g, 2.50 mmol), and 3 (0.397 g, 2.00 mmol) (all added as 2.14 mL of a 5.00:2.50:2.00M 1:2:3 solution), 4 (123 mg, 0.500 mmol, added as 0.760 mL of a 660 mM suspension in DMF), ethyl-2(phenylcarbanothioylthio)-2-phenylacetate (5.5 mg, 0.018 mmol) and AIBN (0.8 mg, 0.005 mmol) (added as 0.38 mL of a 46 mM RAFT:13 mM AIBN solution in DMF), trioxane (55 mg, 0.61 mmol, added as 0.090 mL of a 6.66 M solution in DMF), and 1.63 mL of DMF to a final reaction volume of 5.0 mL.

2. 50% Conversion Target (B1, B2, B3, B4)

4 clean 20 mL glass ampules were each charged with 1 (0.501 g, 5.00 mmol), 2 (0.125 g, 2.50 mmol), and 3 (0.397 g, 2.00 mmol) (all added as 2.14 mL of a 5.00:2.50:2.00M 1:2:3 solution), 4 (123 mg, 0.500 mmol, added as 0.760 mL of a 660 mM suspension in DMF), ethyl-2(phenylcarbanothioylthio)-2-phenylacetate (11 mg, 0.035 mmol) and AIBN (1.6 mg, 0.010 mmol) (added as 0.76 mL of a 46 mM RAFT:13 mM AIBN solution in DMF), trioxane (55 mg, 0.61 mmol, added as 0.090 mL of a 6.66 M solution in DMF), and 1.25 mL of DMF to a final reaction volume of 5.0 mL.

3. 75% Conversion Target (C1, C2, C3, C4)

4 clean 20 mL glass ampules were each charged with 1 (0.501 g, 5.00 mmol), 2 (0.125 g, 2.50 mmol), and 3 (397 mg, 2.00 mmol) (all added as 2.14 mL of a 5.00:2.50:2.00M 1:2:3 solution), 4 (123 mg, 0.500 mmol, added as 0.760 mL of a 660 mM suspension in DMF), ethyl-2(phenylcarbanothioylthio)-2-phenylacetate (16.6 mg, 0.052 mmol) and AIBN (2.5 mg, 0.015 mmol) (added as 1.14 mL of a 46 mM RAFT:13 mM AIBN solution in DMF), trioxane (55 mg, 0.61 mmol, added as 0.09 mL of a 6.66 M solution in DMF), and 0.87 mL of DMF to a final reaction volume of 5.0 mL.

Each reaction mixture was degassed by 4 freeze-pump-thaw cycles and the ampules were flame sealed at 30 mtorr. The ampules were held in an 80° C. oven for the total number of hours as listed: (A1: 18.25 h A2; 18.25 h A3: 2 h A4: 5.8 h B1: 18.25 h B2: 20.3 h B3:23.3 h B4: 5.8 h C1: 5.8 h C2: 14.5 h C3: 14.5 h C4: 14.5 h). Each viscous mixture was cooled in liquid nitrogen and then cracked open. The polymer was precipitated by dropwise addition of the diluted mixture into 250 mL of stirring pentane. The pink-purple precipitate was then dissolved in 10 mL of water and transferred to a 3500 MWCO centrifuge filter. Each sample was washed 5 times via spinning the solution down to a total volume of 2 mL and bringing it back up to 10 mL via addition of fresh water. The resulting solution was then transferred to a vial and dried under vacuum overnight.

Individual monomer conversion was calculated from $^{13}C$ NMR using the polymerization solvent (DMF carbonyl at 162.37 ppm) as the internal standard. Monomers MMA (136.25 ppm) and OEGMA (136.33 ppm) could be resolved individually. Monomers 2-EHMA and SPMA could not be resolved from each other (136.55 ppm) and are grouped in the calculations of the conversion.

Global monomer conversion was calculated from the individual monomer conversions together with the total monomer composition. Plotting the individual conversions against these total conversions for all samples reveals a slower consumption of MMA in comparison to the other monomers, as expected with the lower reactivity reported for MMA in copolymerizations with methylene methacrylate esters, including OEGMA. This suggests a slight drift from the starting monomer composition of 50% to 54-56% MMA, remaining at that level to at least 70% conversion. This indicates a minimal drift in copolymer composition and is further corroborated by the near-perfect overlapping in the superimposition of the $^1H$ NMR of the purified polymers at all conversions.

Section S3. All-Atom Molecular Dynamics Simulations
S3.1. Simulations Methodology The classical molecular dynamics (MD) simulations were performed at the all-atom resolution using the package GROMACS (version 5.0) (32). The CHARMM 36 force field (33, 34) and the compatible CHARMM General Force Field (CGenFF) (35, 36) were used for all the molecules investigated, which has already been implemented in GROMACS (33). The CHARMM 36 force field has been well established in investigating macromolecule (both natural and synthetic) systems (37).

The structure of the protein HRP was downloaded from the RSCB Protein Data Bank with the protein ID 1H55. The degree of polymerization (DP) of 80 is employed for the RHP, which is close to the experimental molar weight of 20 kDa (DP is around 88). In building a single RHP chain, random seeds were varied to match the experimental composition ratio of MMA:2-EHMA:OEGMA:3-SPMA=10:4:5:1. Therefore, each polymer chain contained 40 MMA, 16 2-EHMA, 20 OEGMA and 4 3-SPMA monomers in a random order. In total, 12 different RHP chains were built using different random seeds so that the ratio of the concentration of polymer to that of protein matched the experimental value. To investigate the influence of solvent on the encapsulation of proteins by RHPs two different solvent conditions, aqueous solution and organic (toluene) solution were studied. The compositions of the components are provided in Table S3.

Due to the nature of long polymer chains, the encapsulation kinetics is beyond the capability of atomistic MD simulations. Therefore, some approaches were employed to speed up the polymer-protein aggregation process. In specific, the simulation was first performed in vacuum condition, followed by the simulations at an elevated temperature of 400 K before the production simulation at room temperature (298 K).

The initial structures of the polymer-protein complex were built using the package PACKMOL (38). The protein molecule was initially put in the center of the box with the edge length of 15 nm in all dimensions. The 12 polymer chains were subsequently arranged surrounding the protein with one out of the four —$SO_3^-$ groups distributed within the distance of 4 nm from the center of mass of the protein molecule. Note the size of the protein molecule is around 6×4×4 $nm^3$. After a short energy minimization using the steepest descent algorithm, the polymer-protein complex was simulated under vacuum conditions for a duration of 1 ns. At the end of the simulation, all the polymer chains were aggregated surrounding the protein molecule. In the simulation under the vacuum condition, the NTV ensemble (constant number of particles, temperature and volume) was employed via the V-rescale thermostat (the reference temperature 400 K and the characteristic time of 0.5 ps). The backbone atoms of the protein molecule were constrained at their initial coordinate using a force constant of 1000 $KJ/mol/nm^2$ to maintain the structure of the protein molecule.

Based on the final frame of the simulation under vacuum condition, the polymer-protein complex was subsequently embedded in organic toluene solution or water solution. See Table S3 for the number of solvent molecules added. They were used as the initial structures for the following simulations under the organic or the aqueous solutions. In the following simulations, the periodic boundary conditions were imposed in all the three dimensions; neighbor searching was performed for a distance up to 1.2 nm, and was updated every 10 time steps; the short-range van der Waals interactions using the Lennard-Jones (LJ) 12-6 potential were truncated at 1.2 nm with the long-range dispersion corrections applied for both the energy and the pressure; the short-range Coulomb interactions was also truncated at 1.2 nm with the long-range interactions calculated using the smooth Particle Mesh Ewald algorithm (39, 40). Moreover, to speed up the simulations, the simulation time step of 2 fs was employed by constraining the covalent bonds involving hydrogen atoms using the LINCS algorithm (41, 42). To speed up the process for the optimal polymer-protein aggregate structure, the simulations were first simulated at a temperature of 400 K, which served as a simple means to enhance the simulation sampling of protein-polymer aggregation. The NTP ensemble (constant number of particle, temperature and pressure) was applied with the temperature coupled via V-rescale algorithm and the isotropic Berendsen barostat (the reference pressure 1 bar). The simulation duration of 40 ns was performed, during which the protein backbone atoms were again constrained to maintain the structure.

The production simulations were subsequently performed at room temperature of 298 K. The position restrain was switched off for the protein molecule, allowing it to fully relax for the optimal structure. The NTP ensemble was imposed with the pressure coupled via the Parrinello-Rahman algorithm (reference pressure 1 bar, characteristic time 4 ps, compressibility of $4.5 \times 10^{-5}$ $bar^{-1}$). The temperatures of protein, polymer and solvent (toluene, or water) were separately coupled via the Nose-Hoover algorithm (reference temperature 298 K, characteristic time 0.5 ps). The frames were saved at a frequency of 50 ps. The toluene system was simulated for a duration of 600 ns with the last 400 ns employed for the data analysis. The water system was simulated 200 ns.

To justify the convergence of the all-atom MD simulations, we calculated the radius of gyration ($R_g$) and the root mean square deviation (RMSD) of the backbone atoms of both protein HRP and the 12 polymer chains in the toluene solution simulations at 400 K and 298 K. Similar calculations were performed for the water solution simulation. Furthermore, we calculated the system potential energies and densities in the two systems as a function of the simulation time. The obtained results support the convergence of protein-polymer aggregation behavior in the toluene and water solution simulations. Note that longer simulations at the microsecond or beyond, or enhanced sampling approaches (e.g., metadynamics (43, 44), replica-exchange (45)), could provide further evidences in terms of the convergence of the all-atom simulations. Nevertheless, these methods are highly computationally expensive for complex, large-length-scale simulations, like the protein-polymers aggregates investigated here.

S3.2. Control all-Atom Simulation Justifying the CHARMM36 Force Field

In addition to the three systems aforementioned, a control simulation was performed. In the control system, one protein molecule was solved in the water solution in addition to the ligand molecules of HEME-Fe, acetate ion, $Ca^{2+}$ ions and 403 water molecules. See also Table S3. All the simulation parameters were the same as those in the production simulations at 298 K presented above. The convergences of the calculated secondary structures and the RMSD of the protein backbone atoms justify the employment of the CHARMM36 force field.

S3.3. Protein Encapsulation

The protein-polymer complexes are forming core-shell structures, where protein 1H55 is encapsulated by the polymers.

S3.4. Secondary Structures of Protein HRP

The secondary structures of the protein 1H55 residues (Table S4) are calculated based on the STRIDE method under the VMD package (46).

S3.5. Correlation Between Protein Surface Residues and their Nearest Polymer Neighbors in Toluene To quantify the correlations between the protein surface and the surrounding polymer monomers, the protein surface residues, as well as the surrounding polymer monomers, are classified to be hydrophilic and hydrophobic. For the protein, the following residues are considered as hydrophobic: ALA, GLY, ILE, LEU, MET, PHE, PRO, TRP, TYR and VAL, while all other protein residues are considered hydrophilic. For the polymer, the MMA and 2-EHMA monomers are considered hydrophobic, and OEGMA and 3-SPMA monomers are hydrophilic.

First, the protein backbone atoms on the surface are labeled by assuming that the protein is in the roughly spherical shape. To that end, all the protein backbone atoms are searched. An imaginary spherical shell of the radius of 5 nm (larger than the protein radius) is implicitly included based on the center of mass (COM) of the protein backbone atoms $(x_c, y_c, z_c)$. For each polymer backbone atom located at $(x, y, z)$, the nearest position $(x_s, y_s, z_s)$ on the spherical shell is obtained based on the vector from the protein COM $(x_c, y_c, z_c)$ to the protein backbone atom $(x, y, z)$. Then all the protein backbone atoms are searched so as to find the nearest one to the position on the shell $(x_s, y_s, z_s)$, which is consequently labeled as a protein surface atom. Based on all the labeled protein surface atoms, the hydrophilic/hydrophobic features of the protein surface are counted quantitatively.

Based on the labeled protein surface atoms, those polymer tail atoms are marked which are the nearest-neighbors of the protein surface atoms labeled in the previous step. In these calculations, the last hydrocarbon atoms on the tails of MMA and 2-EHMA monomers, the last oxygen atoms on OEGMA and the sulfur atom on 3-SPMA monomers are employed. With MMA and 2-EHMA defined as hydrophobic, OEGMA and 3-SPMA defined as hydrophilic, the hydrophilic and hydrophobic features of the polymer neighbors to the labeled protein surface atoms are consequently defined.

Based on the hydrophilic and hydrophobic nature of the protein surface atoms and of their nearest-neighbor polymer tail atoms, the numerical probabilities of the correlations between the hydrophilic and hydrophobic protein surface and the hydrophilic and hydrophobic polymer neighbors are quantitatively calculated.

Similar to Step 3, the intermolecular (Coulomb and LJ 12-6) interaction energies between the protein surface residues and their polymer neighbor residues are thus calculated.

Section S4. Coarse-Grained Model and Simulations

We developed a coarse-grained model and simulation based on the all-atom model and results obtained from Section S4. Specifically, we took the final HRP configuration equilibrated in toluene and created a shape-based coarse-grained model using the CGBuilder plugin in the VMD software package (47, 48). The atoms in the hydrophobic residues are coarse-grained into 98 spherical beads and those in the hydrophilic residues into 107 spherical beads.

The random copolymers are modeled as linear chains consisting of P=20 beads of 4 types A, B, C and D, corresponding to monomers MMA, 2-EHMA, OEGMA and 3-SPMA, respectively. The bonds between consecutive beads in a chain are connected via finitely extensive non-linear elastic (FENE) springs. Despite its simplicity, the linear chain model proves to be sufficient for qualitatively capturing the adsorbing behavior of the polymers on the protein surface observed in our all-atom MD simulations and experiment.

In developing the present CG model, we choose to focus on the competition between the short-ranged attractions between polymer beads and between polymer beads, leaving electrostatic interactions for future studies. This is reasonable for the present study because the fraction of the charged residues on the HRP surface under experimental conditions is presumably small. As such, the interaction between the adsorbing polymer beads (i.e. of types A and B) and polymer attractive sites is modeled by the 12-6 Lennard-Jones (LJ) potential, of which the energy well depth, $\varepsilon_{Hh}$, characterizes the adsorption strength. The solvent selectivity is modeled by the effective attraction between the polymer beads of types A and B themselves via the LJ potential with the energy well depth $\varepsilon_{hh}$. The LJ potentials are truncated and shifted to zero at the cutoff distance of $3.0\sigma$. The effective interactions between other bead types are modeled by the purely repulsive Weeks-Chandler-Andersen (WCA) potential.

The CG simulations are performed at constant temperature and volume using the Langevin thermostat. The solvent molecules and counterions are treated implicitly and their effects are modeled by the random and drag forces applied to individual beads by the Langevin thermostat. The equation of motion of individual CG beads is governed by:

$$ma = F_C + F_D + F_R$$

where m and a are the bead mass and acceleration, respectively; $F_C$ is the conservative force, $F_D = -\gamma v$ is the drag force, and $F_R$ is the random force, whose magnitude is proportional to $(k_B T\gamma/\Delta t)^{1/2}$ according to the fluctuation-dissipation theorem. The simulation time step is $\Delta t=0.005\tau$, where t is the dimensionless time unit $\tau = \sigma(m/\varepsilon)^{1/2}$, where m=1 is the mass of the CG beads and $\varepsilon=1$ is the energy well depth of the WCA potential. The dimensionless set temperature is $T^* = k_B T/\varepsilon = 1.0$. All the CG simulations were performed using LAMMPS version 20 Sep. 2016 (49). The protein is located at the center of the cubic simulation box whose dimension is $L=65\sigma$ with periodic boundary conditions.

The protein beads are constrained to their equilibrated configurations via harmonic springs to ensure that the global structure of the protein is maintained while taking into account the effects of thermal fluctuations due to implicit solvent and counterion bombardments. We vary the number of polymer chains $N_C$=12, 50 and 100, to cover the molar ratios used in experiment and that in all-atom MD simulation ($N_C$=12). The total number of CG beads varies from N=445 to 2205. The random order of the monomers within the chains is generated by two methods: 1) the bead types are shuffled within individual chains and 2) the bead types are shuffled within the total number of polymer beads. The first method is used when the number of chains $N_C$ is sufficiently large, e.g. $N_C$=50 and 100. The second method is used when the number of chains is small, i.e. $N_C$=12, so as to improve the randomness in the monomer order. The compositions of beads of types B and D are always fixed at 0.2 and 0.05, respectively, consistent with those in full-atom MD simulations. When the composition of beads of type A, $\phi_A$, is varied, the composition of beads of type C is adjusted accordingly to ensure that $\phi_A+\phi_B+\phi_C+\phi_D=1$.

To accelerate the sampling of the adsorption process by MD simulations, we constrain all the polymer chains within a spherical volume of radius $R_c$ using harmonic springs (i.e. using the command fix indent in LAMMPS). The value of $R_c$ is chosen so that the number density of the polymer beads in the spherical confinement is fixed at $0.1\sigma^{-3}$ for all the polymer-protein molar ratios studied. The choice of such a number density is motivated by our all-atom MD simulations and experimental conditions.

To ascertain that the simulation results are not biased by initial configurations, we vary the random seeds used to generate the random polymer chains and the initial velocity profiles of the polymer beads. To further improve the statistics of the simulation results, we perform annealing/equilibrating cycles for each data point. During the annealing period, the interaction between the polymer attractive sites and polymer adsorbing beads is switched to the purely repulsive WCA potential so that the system is annealed at the athermal condition before being equilibrated again. In addition to monitoring the system potential energy, we also measure the average number of adsorbing polymer sites in the vicinity of each attractive site to justify if the equilibration reaches steady state. At the end of the equilibration period, the final configuration is then collected for analyzing surface coverage, pair correlation functions and radial density profiles. By using annealing/equilibrating cycles, we attempt to avoid kinetically trapped configurations with strong attractions, as well as to obtain statistically uncorrelated final configurations.

We have also run additional Hamiltonian exchange simulations to assure the system is equilibrated at equilibrium. In the Hamiltonian exchange simulations, we used 16 replicas each assigned with an adsorption strength $\varepsilon_{Hh}$ in the range of 0.3-1.8 $k_BT$. A trial swap in $\varepsilon_{Hh}$ between adjacent replicas is attempted every $10^4$ time steps. The swap is accepted or rejected using a Metropolis-like criterion (1). A replica-exchange simulation for a given value of $\phi_A$ is performed for 50 million time steps. The configurations obtained at each value of $\varepsilon_{Hh}$ are then collected at the end of the run from the replicas for surface coverage analysis. The results from the Hamiltonian exchange runs are indeed consistent with those obtained from the heating/cooling procedure, as already reported.

We estimate surface coverage $\Gamma$ from particle-based molecular simulation data as follows. First, the protein beads that interact with the polymer beads are identified. The maximum distance from the protein beads to the center of mass of the protein $r_{max}$ is then calculated. Next, we construct a spherical volume of radius $(r_{max}+r_c)$ centered at the protein center of mass, and divide the spherical surface into $N_{cells}$ with equal areas so that the dimension of each cell is approximately $\sigma$. The polymer beads that are within the spherical volume are then binned into the cells based on their coordinates. The ratio between the number of the occupied cells and the total number of cells $N_{cells}$ gives the approximate measure of surface coverage $\Gamma$.

We determined the representative final configurations for different adsorption strengths, $\varepsilon_{Hh}$, when the attraction between the beads of type A and B is fixed at $\varepsilon_{hh}=0.8k_BT$ and the fraction of A is $\phi_A=0.5$.

We also demonstrated that the pair correlation functions between adsorbed polymer beads for different fractions of the adsorbing components $\phi_A$ and between the attractive sites of the protein. The increase in the peak height of the pair correlation function with $\phi_A$ strongly correlates with the surface coverage, indicating that the polymer adsorbed beads are more likely to match the distribution of protein attractive sites upon increasing the composition of the adsorbing components.

Our simulation results reveal that surface coverage increases with the polymer-ratio molar ratio for all the adsorption strength studied. This is because $N_C$ is proportional to the number of adsorbing beads, which to a certain degree have similar effects to increasing $\phi_A$.

The structural properties of the polymer chains are investigated. The variation in the number of adsorbed polymer chains, $n_{ads}$, as functions of $\phi_A$ and adsorption strength $\varepsilon_{Hh}$ was determined. Upon increasing $\phi_A$, $n_{ads}$ increases because there are more adsorbing polymer beads, as expected. Nevertheless, at higher values of $\phi_A$, $n_{ads}$ is reduced for strong attractions between polymer beads of types A and B. The strong correlation between $n_{ads}$ and surface coverage $\Gamma$ can be explained as follows. In the one hand, $n_{ads}$ is proportional to the energetically favored polymer-protein contacts governed by the adsorption strength. Consequently, $n_{ads}$, and hence $\Gamma$, increases with $\phi_A$ and the density and distribution of the protein attractive sites. On the other hand, $n_{ads}$ characterizes with the entropic loss due to the surface confinement of the chains, compared to those that are not adsorbed. The entropic loss is reduced when $\varepsilon_{hh}$ increases because the polymer beads of types A and B that are not non-adsorbed tend to aggregate. The optimal value of $\Gamma$ and the maximum value of $n_{ads}$ are then attributed to the competition between the tendency of the polymers to avoid entropic loss due to confinement to the surface and their tendency to maximize their energetically favored contacts.

Our structural analysis of the adsorbed polymer chains shows the pair correlation functions of the adsorbing beads and polymer attractive sites for different adsorption strengths, which are consistent with the findings from our all-atom MD simulations in Section S3. Our results further show the radial density profiles of the polymer beads from the protein center of mass for different adsorption strengths. The peak of the density profiles shifts to higher values and gets closer to the protein surface as $\varepsilon_{Hh}$ increases.

Section S5. RHP-Mediated Cell Free Synthesis and Protein-RHP Complexes

Cell-Free Protein Synthesis.

Cell-free protein synthesis was performed according to PURExpress manual with modifications. Briefly, in a 25 µl reaction, RHP was added to the ribosome solution in a ratio of 50/1 (mole/mole), and incubated on ice for 30 min. The polymer/ribosome samples were mixed with solution A and B containing all other required enzymes, RNAs, energy and nutrient molecules. 20 units RNase inhibitor and 200 ng plasmids for PepTso-GFP, PepTso, or AqpZ-GFP were added, and the mixtures were incubated at 37° C. for 3 hours to complete membrane protein synthesis. The resulting samples were stored at −20° C.

Kinetics of Protein Synthesis and Western Blot Analysis.

Kinetics of PepTso-GFP and A Z-GFP cell-free synthesis were monitored through measuring the fluorescence intensity of the GFP tag on a Tecan I-control infinite 200 plate reader. Cell-free protein synthesis mixtures were incubated in 384-well plate at 37° C., and the GFP fluorescence (Ex/Em 480 nm/520 nm) was recorded over 3 hours. For the western blot, proteins in the cell-free protein synthesis samples were first separated by sodium dodecyl sulfate polyacrylamide gel electrophoresis (SDS-PAGE). Lane 1 corresponds to protein mass standards. (Spectra multicolor broad range protein ladder, (ThermoFisher)) The proteins were then electrophoretically transferred to a polyvinylidene difluoride (PVDF) membrane. Multicolor protein mass standards were visible on the membrane after successful transfer. The membrane was then blocked with 3% BSA, incubated with 1:2000 mouse anti-GFP antibody, and washed. Following incubation with 1:4000 alkaline phosphatase conjugated goat anti-mouse secondary antibody, band colors were developed by using 5-bromo-4-chloro-3-indolyl phosphate (BCIP) and nitroblue tetrazolium (NBT).

Reconstitution of Membrane Protein and Transport Assay.

The preparation of POPE/POPG (3/1) proteoliposomes containing PepTso was performed following the reported method with modifications (26). Briefly, to prepare liposomes, chloroform in lipid was evaporated, and resulting lipid film was further dried under vacuum overnight. Dried lipid film was solubilized at 10 mg/mL in an inner solution (5 mM HEPES pH 6.8, 1.2 mM NaCl, 120 mM KCl, 2 mM $MgSO_4$, 1 mM pyranine) at 37° C. for 1 hour. 10 μL of the cell-free PepTso synthesis mixtures was added to 500 μL of the liposomes solutions, which was then subjected to 6 cycles of freeze/thaw using liquid nitrogen and 37° C. water bath. The resulting proteoliposomes were extruded 10 times through 0.4 μm membranes at 37° C. Excess pyranine was removed through a sephadex G-25 desalting column using the inner solution without pyranine. Before proton and oligopeptide transport assay, samples containing the proteoliposomes were diluted 20 folds in the outer solution (5 mM HEPES pH 6.8, 1.2 mM KCl, 120 mM NaCl, 2 mM $MgSO_4$) containing 0.2 mM dipeptide Ala-Ala. 1 μM valinomycin was added to the outer solution to initiate the proton transport. Proton transport was measured by reading the ratio of pyranine fluorescence at 510 nm when excited at 460 and 415 nm (51) in a cuvette with a stirring magnetic flea, on a Perkin Elmer LS55 Fluorescence spectrometer.

Horseradish peroxidase type II (HRP, Sigma-Aldrich) and glucose oxidase type II (GOx, Sigma-Aldrich) were dissolved in Milli-Q water (Millipore) to a concentration of 10 mg/mL. α-chymotrypsin (α-CT, Sigma-Aldrich) was dissolved in 0.1 M Tris-HCl with 1 mM $CaCl_2$, pH 7.75, to a concentration of 10 mg/mL. Upon arrival of green fluorescent protein (GFP, Millipore), GFP was centrifuge filtrated to remove salts and glycerol using Amicon Ultra-0.5 mL centrifugal filters (Millipore) with a cutoff molecular weight of 10 kDa. GFP was then dissolved in Milli-Q water to a concentration of approximately 1 mg/mL. Organophosphorus hydrolase (OPH) was expressed, based on established procedure. The enzyme was stored in a 50 mM Tris-HCl buffer, pH 9, at a concentration of 1.5 mg/mL. RHPs were dissolved in Milli-Q water at a concentration of 1 mg/mL.

Sodium bis(2-ethylhexyl) sulfosuccinate (AOT, Aldrich) was dissolved in toluene at a concentration of 200 mM. Polymeric surfactant, polystyrene (22 kDa)-block-poly(ethylene oxide) (21.5 kDa) (PS-b-PEO), was purchased from Polymer Source and was dissolved in toluene at a concentration of 1 mg/mL.

To prepare reverse micelles, HRP solutions were injected into AOT solution at a $[H_2O]/[AOT]$ ratio of $w_0=13$ or injected into PS-b-PEO at a volumetric ratio of 1:50 HRP solution to polymer solution. The suspensions were sonicated, mixed, and partially evaporated using a constant stream of $N_2$ gas until optically clear. Additional toluene was added to compensate for evaporated solvent in order to reobtain original concentrations. Protein/RHP complexes were obtained by combining the aqueous RHP solution and protein solution at a volume ratio of 50:1. RHP/protein mixtures were lyophilized overnight, resuspended with toluene to the original concentration, and subsequently sonicated. Other than GFP, all materials were used as received.

S5.2. Structural Characterization

Transmission Electron Microscopy (TEM)

RHP-HRP complexes were drop casted on TEM carbon grids (Ted Pella) and dried for 5 minutes. Subsequently, several drops of water were used to wash off excess free polymer. Samples were stained using a 2 w/v % solution of phosphotungstic acid in water for 2 minutes. TEM images were taken on a JEOL 1200EX TEM at an accelerating voltage of 80 kV. In toluene HRP/RHP forms nanoparticles, ~50 nm in size.

Fourier-Transform Infrared Spectroscopy (FT-IR)

To enhance the signal-to-noise ratio, solutions of HRP/RHP complex were concentrated to reach a HRP concentration of ~8-10 mg/mL. Solutions were deposited in a liquid cell composed of $CaF_2$ windows with a path length of 1 mm Spectra were collected at 0, 2, 4, 8, and 24 hours after resuspension in toluene on a Thermo Scientific Nicolet 6700. Measurements were conducted at room temperature and the amide I band between $1700 \text{ cm}^{-1}$ and $1620 \text{ cm}^{-1}$ was monitored. Spectral analysis was performed using the built-in OMNIC Spectra Software.

UV-Visible Spectroscopy (UV-Vis)

UV-visible spectroscopy was performed on a Hewlett-Packard 8453 Spectrophotometer. HRP/RHP complex solutions in toluene were sealed in a 1-cm path length quartz cuvette. Measurements were conducted at room temperature and the location of the hemin peak was monitored between 350 nm and 800 nm at 0, 2, 4, 8, and 24 hours after resuspension.

Fluorescent Spectroscopy

Retention of GFP fluorescence was evaluated using a Perkin Elmer LS-55 fluorescence spectrometer Immediately after dissolving GFP/RHP in toluene, solutions were sealed in a 1-cm path length quartz cuvette and excited at an excitation wavelength of 450 nm. Emission wavelength was monitored between 450 nm and 600 nm. Measurements were conducted at room temperature and taken at 0, 2, 4, 8, and 24 hours after resuspension in toluene.

S5.3. Assay of Protein Activity in Aqueous Buffer

Solutions were left in ambient room temperature conditions for 0, 2, 4, 8, and 24 hours in toluene. After specified times, aliquots were taken and diluted in 100 mM $KH_2PO_4$/$K_2HPO_4$ phosphate buffer, pH 6, to disperse the protein and RHP. After thorough mixing, the assay solution is applied. Activity was quantified using UV-visible spectroscopy by monitoring the conversion of the colorimetric assay.

HRP activity was assessed using a TMB Peroxidase EIA Substrate Kit (Bio-Rad). Baseline HRP activity was determined by preparing a stock protein solution in 100 mM $KH_2PO_4/K_2HPO_4$ phosphate buffer at pH 6 and applying a prepared TMB assay solution, as outlined by the manufacturer. Solution was thoroughly mixed and UV-visible spectroscopy was performed on a Hewlett-Packard 8453 Spectrophotometer. A 1-cm path length cuvette was used and absorbance at 370 nm was monitored.

GOx activity was assessed using an assay containing glucose, phenol, 4-aminoantipyrine, and HRP. Baseline GOx activity was determined by preparing a stock protein solution in 100 mM $KH_2PO_4/K_2HPO_4$ phosphate buffer at pH 6 and applying the colorimetric assay. A 1-cm path length cuvette was used and absorbance at 505 nm was monitored.

OPH activity was assessed using an assay containing methyl parathion. Baseline OPH activity was determined by preparing a stock protein solution in 50 mM TRIS-HCl buffer and applying the colorimetric assay. OPH activity was monitored using a Thermo Fisher Scientific NanoDrop 2000 at 405 nm.

S5.4. Evaluation of RHP-Assisted Protein Dispersion and Stabilization for Other Proteins

GFP

Similar experiments were performed using GFP and fluorescence was monitored as a function of incubation time in toluene.

GOx PEGylation was performed following the procedure reported previously. (28) The feeding ratio of PEG was adjusted to increase PEGylation.

S5.5. Protein-Containing Fiber Mats

Electrospinning

For PMMA based electrospun fiber mats, poly(methyl methacrylate) (PMMA, Sigma-Aldrich) ($M_w$=350,000 g/mol) was first dissolved in chloroform to achieve a 7.5 wt % solution concentration. 200 µL of toluene containing the protein/RHP complex was mixed with 800 µL of the PMMA/chloroform solution. For present studies, the protein concentration in the fiber mat is typically in the range of 0.3-0.5 wt %. The mixture was stirred for 5 minutes at 350 RPM immediately prior to electrospinning. The solution was then electrospun from a 1 mL syringe and a 20 gauge needle. An aluminum collector plate was placed 18 cm away from the needle tip in a horizontal setup. The solution was pumped at a rate of 0.45 mL/hr. A voltage of 8 kV was applied to the solution. For PEO-based fiber mats, OPH-RHP was lyophilized and resuspended directly into a 5.5 wt % PEO ($M_w$=900,000 g/mol) in MilliQ water solution. A flat aluminum collector plate was placed 20 cm from the needle tip. An accelerating voltage of 9 kV was applied to the solution, which was pumped at a flow rate of 0.35 mL/hr.

Scanning Electron Microscopy (SEM)

A Hitachi TM-1000 scanning electron microscope was used to acquire images of the electrospun fibers. The samples were mounted on conductive carbon tape. A 15 kV accelerating voltage was used to acquire the SEM images.

Assay of OPH Activity in Electrospun Fibers

Protein/RHP-loaded fiber mats were tested in the same aqueous buffer used to measure activity of free proteins. The activity was monitored visually by the solution color change. A protein loading of approximately 1 µg of OPH per 1 mg of polymer was achieved.

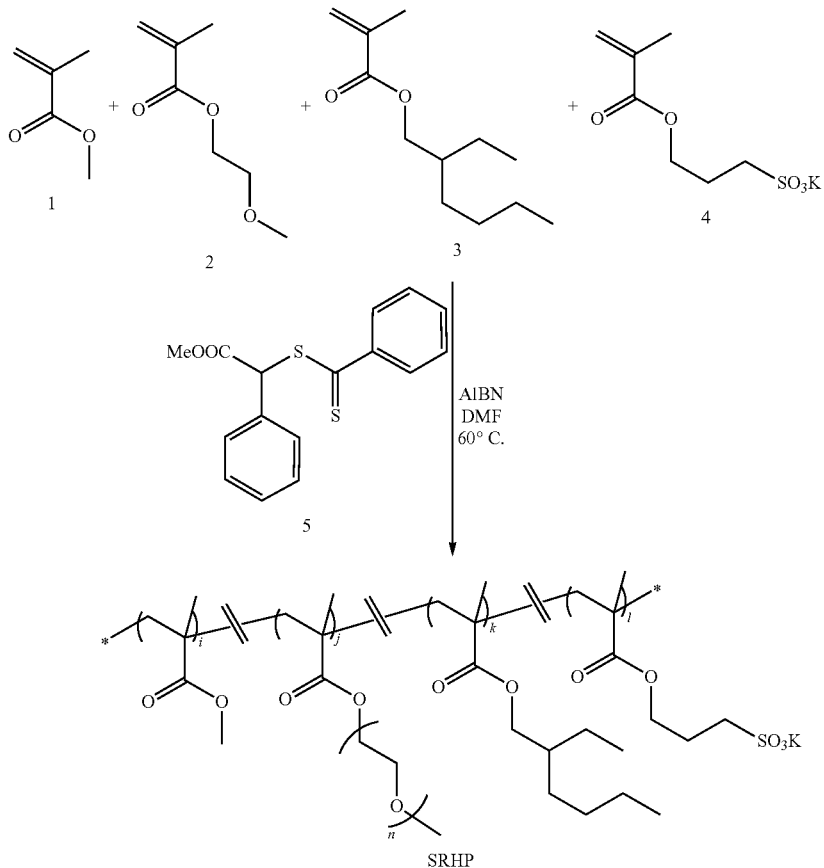

Synthesis of RHP by RAFT Polymerization.

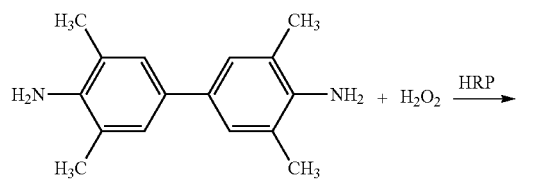

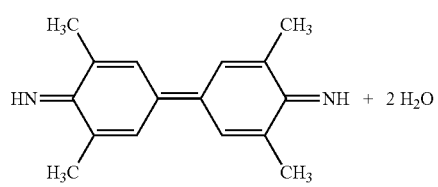

Colorimetric Assay to Evaluation HRP Activity.

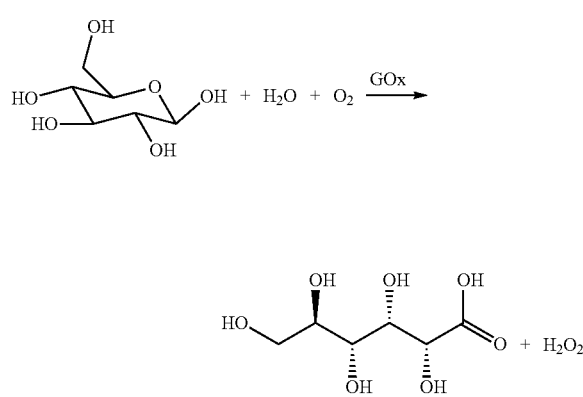

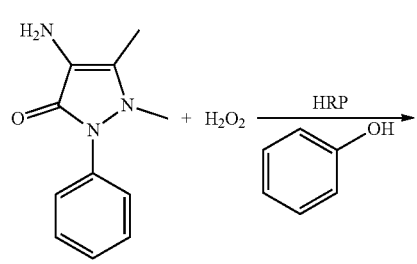

Colorimetric Assay to Evaluation GOx Activity.

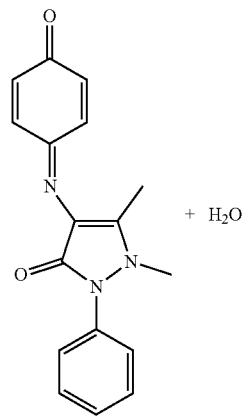

Colorimetric Assay to Evaluation OPH Activity.

TABLE S1

Reactivity ratios used in 4-monomer copolymerization simulation.

| | MMA | OEGMA | EHMA | SPMA |
| --- | --- | --- | --- | --- |
| MMA | 0.89 | 1 | 1 | 1 |
| OEGMA | 1 | 1.09 | 1.09 | 1.09 |
| EHMA | 1 | 1.09 | 1.09 | 1.09 |
| SPMA | 1 | 1.09 | 1.09 | 1.09 |

TABLE S2

Physico-chemical properties of RHP.

| mol % of 1 | mol % of 2 | mol % of 3 | mol % of 4 | $M_n^a$ (kg/mol) | $Ð^a$ |
| --- | --- | --- | --- | --- | --- |
| $50/46^b$ | $25/32^b$ | $20/18^b$ | $5/4^b$ | 30.2 | 1.38 |

$^a$Determined by SEC.
$^b$Theoretical/experimental mol % determined by gravimetry and quantitative $^{13}C$ NMR, respectively.

TABLE S3

Compositions of HRP/RHP Mixtures in the Different All-Atom MD Simulations.

| | protein [a] | polymer [b] | toluene [c] | water [c] |
|---|---|---|---|---|
| vacuum | 1 | 12 | — | — |
| aqueous solution | 1 | 12 | — | 92151 |
| organic solution | 1 | 12 | 15430 | — |
| control | 1 | — | 0 | 31246 |

[a] Protein contains one 1H55 molecule and its ligands of HEME-Fe, acetate ion, $Ca^{2+}$ ions and 403 water molecules.
[b] 12 polymer chains with DP = 80, and 48 $K^+$ counterions.
[c] Solvent: toluene or water.

TABLE S4

Probabilities (%) of Secondary Structures in the Three Different All-Atom Simulations

| | β-sheet | Coil | Turn | α-helix | 3-10 helix |
|---|---|---|---|---|---|
| Control simulation | 4.4 ± 0.6 | 19 ± 1 | 27 ± 2 | 47 ± 1 | 3 ± 1 |
| toluene solution | 4.4 ± 0.6 | 19 ± 1 | 26 ± 2 | 47 ± 1 | 4 ± 1 |
| aqueous solution | 4.4 ± 0.7 | 19 ± 1 | 28 ± 2 | 47 ± 1 | 2 ± 1 |

REFERENCES

1. A. M. Klibanov, Improving enzymes by using them in organic solvents. *Nature* 409, 241-246 (2001).
2. J. L. Popot et al., Amphipols: polymeric surfactants for membrane biology research. *Cellular and Molecular Life Sciences* 60, 1559-1574 (2003).
3. E. M. Pelegri-O'Day, H. D. Maynard, Controlled Radical Polymerization as an Enabling Approach for the Next Generation of Protein-Polymer Conjugates. *Accounts of Chemical Research* 49, 1777-1785 (2016).
4. R. B. Bhatia, C. J. Brinker, A. K. Gupta, A. K. Singh, Aqueous sol-gel process for protein encapsulation. *Chem Mater* 12, 2434-2441 (2000).
5. K. A. Dill, Dominant Forces In Protein Folding. *Biochemistry* 29, 7133-7155 (1990).
6. J. Y. Shu et al., Amphiphilic Peptide-Polymer Conjugates Based on the Coiled-Coil Helix Bundle. *Biomacromolecules* 11, 1443-1452 (2010).
7. N. Dube, A. D. Presley, J. Y. Shu, T. Xu, Amphiphilic Peptide-Polymer Conjugates with Side-Conjugation. *Macromolecular Rapid Communications* 32, 344-353 (2011).
8. R. Lund, J. Shu, T. Xu, A Small-Angle X-ray Scattering Study of alpha-helical Bundle-Forming Peptide-Polymer Conjugates in Solution: Chain Conformations. *Macromolecules* 46, 1625-1632 (2013).
9. H. J. Dyson, P. E. Wright, Intrinsically unstructured proteins and their functions. *Nat Rev Mol Cell Bio* 6, 197-208 (2005).
10. Z. R. Liu, Y. Q. Huang, Advantages of proteins being disordered. *Protein Sci* 23, 539-550 (2014).
11. O. D. Monera, T. J. Sereda, N. E. Zhou, C. M. Kay, R. S. Hodges, Relationship of sidechain hydrophobicity and α-helical propensity on the stability of the single-stranded amphipathic α-helix. *Journal of Peptide Science* 1, 319-329 (1995).
12. W. F. DeGrado, C. M. Summa, V. Pavone, F. Nastri, A. Lombardi, De novo design and structural characterization of proteins and metalloproteins. *Annual Review of Biochemistry* 68, 779-819 (1999).
13. D. A. Moffet, M. H. Hecht, De novo proteins from combinatorial libraries. *Chem Rev* 101, 3191-3203 (2001).
14. P. Mansky, Y. Liu, E. Huang, T. P. Russell, C. J. Hawker, Controlling polymer-surface interactions with random copolymer brushes. *Science* 275, 1458-1460 (1997).
15. J. F. Lutz, M. Ouchi, D. R. Liu, M. Sawamoto, Sequence-Controlled Polymers. *Science* 341, 628-631 (2013).
16. J. Chiefari et al., Living free-radical polymerization by reversible addition-fragmentation chain transfer: The RAFT process. *Macromolecules* 31, 5559-5562 (1998).
17. G. Moad, E. Rizzardo, S. H. Thang, Toward living radical polymerization. *Accounts of Chemical Research* 41, 1133-1142 (2008).
18. A. E. Smith, X. Xu, C. L. McCormick, Stimuli-responsive amphiphilic (co)polymers via RAFT polymerization. *Progress in Polymer Science* 35, 45-93 (2010).
19. A. F. M. Barton, *Handbook of Polymer-Liquid Interaction Parameters and Solubility Parameters*. (Taylor & Francis, 1990).
20. J. N. Israelachvili, *Intermolecular and Surface Forces*. (Elsevier Science, 2015).
21. B. G. Manders, W. Smulders, A. M. Aerdts, A. M. vanHerk, Determination of reactivity ratios for the system methyl methacrylate-n-butyl methacrylate. *Macromolecules* 30, 322-323 (1997).
22. F. R. Mayo, F. M. Lewis, Copolymerization I A basis for comparing the behavior of monomers in copolymerization, the copolymerization of styrene and methyl methacrylate. *J Am Chem Soc* 66, 1594-1601 (1944).
23. T. Ge, M. Rubinstein, Strong selective adsorption of polymers. *Macromolecules* 48, 3788-3801 (2015).
24. D. Schwarz et al., Preparative scale expression of membrane proteins in *Escherichia coli*-based continuous exchange cell-free systems. *Nat Protoc* 2, 2945-2957 (2007).
25. A. Muller-Lucks, S. Bock, B. H. Wu, E. Beitz, Fluorescent In Situ Folding Control for Rapid Optimization of Cell-Free Membrane Protein Synthesis. *Plos One* 7, (2012).
26. J. L. Parker, J. A. Mindell, S. Newstead, Thermodynamic Evidence for a dual Transport Mechanism in a POT Peptide Transporter. *eLife* 3, (2014).
27. A. M. Klibanov, Why are enzymes less active in organic solvents than in water? *Trends in Biotechnology* 15, 97-101 (1997).
28. A. D. Presley, J. J. Chang, T. Xu, Directed co-assembly of heme proteins with amphiphilic block copolymers toward functional biomolecular materials. *Soft Matter* 7, 172-179 (2011).
29. B. K. Singh, A. Walker, Microbial degradation of organophosphorus compounds. *Ferns Microbiol Rev* 30, 428-471 (2006).
30. J. K. Grimsley, J. M. Scholtz, C. N. Pace, J. R. Wild, Organophosphorus hydrolase is a remarkably stable enzyme that unfolds through a homodimeric intermediate. *Biochemistry* 36, 14366-14374 (1997).
31. S. Perrier, P. Takolpuckdee, J. Westwood, D. M. Lewis, Versatile Chain Transfer Agents for Reversible Addition Fragmentation Chain Transfer (RAFT) Polymerization to Synthesize Functional Polymeric Architectures. *Macromolecules* 37, 2709-2717 (2004).
32. B. Hess, C. Kutzner, D. van der Spoel, E. Lindahl, GROMACS 4: Algorithms for Highly Efficient, Load-Balanced, and Scalable Molecular Simulation. *J. Chem. Theory Comput.* 4, 435-447 (2008).

33. P. Bjelkmar, P. Larsson, M. A. Cuendet, B. Hess, E. Lindahl, Implementation of the CHARMM Force Field in GROMACS: Analysis of Protein Stability Effects from Correction Maps, Virtual Interaction Sites, and Water Models. *Journal of Chemical Theory and Computation* 6, 459-466 (2010).
34. J. B. Klauda et al., Update of the CHARMM All-Atom Additive Force Field for Lipids: Validation on Six Lipid Types. *J. Phys. Chem. B* 114, 7830-7843 (2010).
35. K. Vanommeslaeghe et al., CHARMM General Force Field: A Force Field for Drug-Like Molecules Compatible with the CHARMM All-Atom Additive Biological Force Fields. *J. Comput. Chem.* 31, 671-690 (2010).
36. W. Yu, X. He, K. Vanommeslaeghe, A. D. MacKerell, Extension of the CHARMM General Force Field to Sulfonyl-Containing Compounds and its Utility in Biomolecular Simulations. *Journal of Computational Chemistry* 33, 2451-2468 (2012).
37. J. Huang et al., CHARMM36m: An Improved Force Field for Folded and Intrinsically Disordered Proteins. *Nature methods* 14, 71-73 (2017).
38. L. Martínez, R. Andrade, E. G. Birgin, J. M. Martínez, PACKMOL: A Package for Building Initial Configurations for Molecular Dynamics Simulations. *J. Comput. Chem.* 30, 2157-2164 (2009).
39. T. Darden, D. York, L. Pedersen, Particle Mesh Ewald: An N·log(N) Method for Ewald Sums in Large Systems. *J. Chem. Phys.* 98, 10089-10092 (1993).
40. U. Essmann et al., A Smooth Particle Mesh Ewald Method. *J. Chem. Phys.* 103, 8577-8593 (1995).
41. B. Hess, P-LINCS: A Parallel Linear Constraint Solver for Molecular Simulation. *J. Chem. Theory Comput.* 4, 116-122 (2008).
42. B. Hess, H. Bekker, H. J. C. Berendsen, J. G. E. M. Fraaije, LINCS: A Linear Constraint Solver for Molecular Simulations. *J. Comput. Chem.* 18, 1463-1472 (1997).
43. A. Laio, M. Parrinello, Escaping Free-Energy Minima. *Proceedings of the National Academy of Sciences of the United States of America* 99, 12562-12566 (2002).
44. A. Barducci, M. Bonomi, M. Parrinello, Metadynamics. *Wiley Interdisciplinary Reviews: Computational Molecular Science* 1, 826-843 (2011).
45. Y. Sugita, Y. Okamoto, Replica-Exchange Molecular Dynamics Method for Protein Folding. *Chemical Physics Letters* 314, 141-151 (1999).
46. W. Humphrey, A. Dalke, K. Schulten, VMD: Visual Molecular Dynamics *J. Mol. Graphics* 14, 33-38 (1996).
47. A. Arkhipov, P. L. Freddolino, K. Schulten, Stability and Dynamics of Virus Capsids Described by Coarse-Grained Modeling. *Structure* 14, 1767-1777 (2006).
48. A. Arkhipov, Y. Yin, K. Schulten, Four-Scale Description of Membrane Sculpting by BAR Domains. *Biophysical Journal* 95, 2806-2821 (2008).
49. S. Plimpton, Fast Parallel Algorithms for Short-Range Molecular Dynamics *Journal of Computational Physics* 117, 1-19 (1995).
50. A. Bunker, B. Dünweg, Parallel Excluded Volume Tempering for Polymer Melts. *Physical Review* E 63, 016701 (2000).
51. Y. Avnir, Y. Barenholz, pH Determination by Pyranine: Medium-Related Artifacts and Their Correction. *Anal Biochem* 347, 34-41 (2005).

The invention claimed is:

1. A method of preserving protein function in foreign environments, the method comprising forming a composition comprising a complex of an active protein and statistically random heteropolymers (SRHPs) in an organic solvent, and detecting activity of the protein in the composition, wherein the SRHPs comprising monomers: methyl methacrylate (MMA), oligo(ethylene glycol) methacrylate (OEGMA), 3-sulfopropyl methacrylate potassium salt (3-SPMA) and 2-ethylhexyl methacrylate (2-EHMA).

2. The method of claim 1, wherein the heteropolymers disperse in both aqueous and organic media.

3. The method of claim 1, wherein a distribution histogram of monomer blocks of the heteropolymers decrease in normalized frequency from block size 1, wherein block size 10 has a normalized frequency of less than 1%, and block size 1 has a normalized frequency of 5-20%.

4. The method of claim 1, wherein the protein is an enzyme or fluorescent protein.

5. The method of claim 1, wherein the solvent is selected from 2-propanol, acetone, acetonitrile, chloroform, dichloromethane, dimethyl sulfoxide, ethyl acetate, hexane, methanol, tetrahydrofuran, and toluene.

6. The method of claim 1, wherein the SRHPs comprising monomers: methyl methacrylate (MMA), oligo(ethylene glycol) methacrylate (OEGMA), 3-sulfopropyl methacrylate potassium salt (3-SPMA) and 2-ethylhexyl methacrylate (2-EHMA), in ratio: 5(MMA):2.5(OEGMA):2(2-EHMA):0.5(3-SPMA).

7. The method of claim 1, wherein:
the protein is an enzyme or fluorescent protein;
the solvent is selected from 2-propanol, acetone, acetonitrile, chloroform, dichloromethane, dimethyl sulfoxide, ethyl acetate, hexane, methanol, tetrahydrofuran, and toluene; and
the SRHPs comprising varying ratios a plurality of monomers selected from methyl methacrylate (MMA), oligo(ethylene glycol) methacrylate (OEGMA), 3-sulfopropyl methacrylate potassium salt (3-SPMA) and 2-ethylhexyl methacrylate (2-EHMA).

8. The method of claim 1, wherein:
the heteropolymers disperse in both aqueous and organic media;
a distribution histogram of monomer blocks of the heteropolymers decrease in normalized frequency from block size 1, wherein block size 10 has a normalized frequency of less than 1%, and block size 1 has a normalized frequency of 5-20%;
the protein is an enzyme or fluorescent protein;
the solvent is selected from 2-propanol, acetone, acetonitrile, chloroform, dichloromethane, dimethyl sulfoxide, ethyl acetate, hexane, methanol, tetrahydrofuran, and toluene; and
the SRHPs comprising varying ratios a plurality of monomers selected from methyl methacrylate (MMA), oligo(ethylene glycol) methacrylate (OEGMA), 3-sulfopropyl methacrylate potassium salt (3-SPMA) and 2-ethylhexyl methacrylate (2-EHMA).

9. The method of claim 1, wherein the protein is organophosphorus hydrolase (OPH).

10. The method of claim 1, wherein the protein and SRHPs are contained in a polymer matrix.

11. The method of claim 1, wherein the protein is organophosphorus hydrolase (OPH), and the protein and SRHPs are contained in a polymer matrix, and the matrix comprises polymerized polyethylene oxide (PEO) or PMMA in the form of a fiber mat.

12. The method of claim 6, wherein the protein is organophosphorus hydrolase (OPH), and the protein and SRHPs are contained in a polymer matrix, and the matrix comprises polymerized polyethylene oxide (PEO) or PMMA in the form of a fiber mat.

13. The method of claim 1, wherein the forming step comprises mixing the protein and the SRHPs in an aqueous solution; drying the mixture; resuspending the dried mixture in the organic solvent, forming the composition.

14. The method of claim 1, wherein the forming step is in a protein expression system, wherein the protein is being expressed and incorporated in the complex, wherein the complex enhances activity of the protein, compared an expression system without the SRHPs.

15. The method of claim 1, wherein the forming step is in a protein expression system, wherein the protein is being expressed and incorporated in the complex, wherein the complex enhances activity of the protein, compared an expression system without the SRHPs and the expression system is a cell-free system.

16. The method of claim 1, further comprising contacting the complex with a liposome under conditions wherein the protein relocates from the complex to the liposome.

17. The method of claim 1, further comprising contacting the complex with a liposome under conditions wherein the protein relocates from the complex to the liposome, in form of an active, transmembrane protein.

\* \* \* \* \*